(12) United States Patent
Nathan et al.

(10) Patent No.: US 12,309,573 B2
(45) Date of Patent: May 20, 2025

(54) PERSONALIZED VERTIGO REHABILITATION

(71) Applicant: SAMSUNG ELECTRONICS CO., LTD., Gyeonggi-Do (KR)

(72) Inventors: Viswam Nathan, Fresno, CA (US); Jilong Kuang, San Jose, CA (US); Jun Gao, Menlo Park, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 219 days.

(21) Appl. No.: 17/566,981

(22) Filed: Dec. 31, 2021

(65) Prior Publication Data

US 2023/0130524 A1    Apr. 27, 2023

Related U.S. Application Data

(60) Provisional application No. 63/271,535, filed on Oct. 25, 2021.

(51) Int. Cl.
| | |
|---|---|
| *H04S 7/00* | (2006.01) |
| *G08B 21/02* | (2006.01) |
| *G16H 15/00* | (2018.01) |
| *G16H 20/30* | (2018.01) |

(52) U.S. Cl.
CPC .............. *H04S 7/303* (2013.01); *G08B 21/02* (2013.01); *G16H 15/00* (2018.01); *G16H 20/30* (2018.01); *H04S 2420/01* (2013.01)

(58) Field of Classification Search
CPC ..... H04S 7/303; H04S 2420/01; G16H 20/30; G16H 15/00; G08B 21/02

USPC ...................................................... 340/573.7
See application file for complete search history.

(56) References Cited

U.S. PATENT DOCUMENTS

| | | | |
|---|---|---|---|
| 9,526,946 B1 * | 12/2016 | Zets .................... | G09B 19/0038 |
| 11,450,113 B1 * | 9/2022 | Vaziri .................... | H04N 7/185 |
| 11,559,252 B2 * | 1/2023 | Burwinkel ............ | A61B 5/1114 |
| 11,638,563 B2 * | 5/2023 | Burwinkel ............ | G08B 21/043 |
| | | | 600/301 |
| 2006/0238877 A1 * | 10/2006 | Ashkenazi ......... | G02B 27/0093 |
| | | | 359/630 |

(Continued)

FOREIGN PATENT DOCUMENTS

CN           213526286 U         6/2021

OTHER PUBLICATIONS

Neuhauser, H.K., "The epidemiology of dizziness and vertigo," Handbook of Clinical Neurology, 2016, vol. 137, pp. 67-82 (Abstract).

(Continued)

*Primary Examiner* — Naomi J Small
(74) *Attorney, Agent, or Firm* — CUENOT, FORSYTHE & KIM, LLC

(57) ABSTRACT

Personalized vertigo rehabilitation and treatment can include generating a sequence of sounds that are modulated to perceptually emanate from one or more distinct locations in three-dimensional space relative to a user. The sequence can be predetermined to guide head movements of the user in a prescribed manner to mitigate vertigo experienced by the user. The user's head movements can be tracked as the user responds to the sequence of sounds. A signal can be conveyed to the user in response to detecting a predetermined head movement by the user.

20 Claims, 8 Drawing Sheets

(56) References Cited

U.S. PATENT DOCUMENTS

| | | | | |
|---|---|---|---|---|
| 2010/0286572 | A1* | 11/2010 | Moersdorf | A61B 5/4519 600/595 |
| 2011/0245235 | A1* | 10/2011 | Hanley | A61P 27/16 514/357 |
| 2016/0081594 | A1* | 3/2016 | Gaddipati | A61B 5/4824 600/595 |
| 2017/0365101 | A1* | 12/2017 | Samec | G06T 19/006 |
| 2018/0075820 | A1* | 3/2018 | Hicks | G06F 3/14 |
| 2018/0317837 | A1 | 11/2018 | Burwinkel et al. | |
| 2018/0359462 | A1* | 12/2018 | Shinohara | G06T 19/00 |
| 2019/0141462 | A1 | 5/2019 | Velati | |
| 2020/0023157 | A1* | 1/2020 | Lewis | A61B 5/369 |
| 2020/0094141 | A1* | 3/2020 | Fersch | H04S 7/302 |
| 2020/0245938 | A1 | 8/2020 | Xu et al. | |
| 2020/0412983 | A1* | 12/2020 | Nakata | H04N 25/443 |
| 2021/0026440 | A1 | 1/2021 | Poupyrev et al. | |
| 2021/0225483 | A1 | 7/2021 | Likovich et al. | |
| 2021/0400399 | A1* | 12/2021 | Gomez | H04R 25/505 |
| 2023/0130524 | A1* | 4/2023 | Nathan | G16H 50/20 340/573.7 |

OTHER PUBLICATIONS

"Vertigo," [online] University of California San Francisco, Conditions and Treatments, © 2002-2021 The Regents of The University of California [retrieved Dec. 31, 2021], retrieved from the Internet: <https://www.ucsfhealth.org/conditions/vertigo>, 3 pg.

"The Connection Between Hearing Loss and Vertigo," [online] © 2021 EarQ [retrieved Dec. 31, 2021], retrieved from the Internet: <https://www.earq.com/hearing-health/articles/connection-between-hearing-loss-and-vertigo>, 2 pg.

Barumerli, R. et al., "Round Robin Comparison of Inter-Laboratory HRTF Measurements—Assessment with an auditory model for elevation," In 2018 IEEE 4th VR workshop on sonic interactions for virtual environments (SIVE) Mar. 2018, pp. 1-5, IEEE.

Zhao, Y. et al., "An Orientation Sensor-Based Head Tracking System for Driver Behaviour Monitoring," Sensors, vol. 17, 2017, No. 11, p. 2692.

Ranjan, R. et al. "Light-Weight Head Pose Invariant Gaze Tracking", Proceedings of the IEEE Conference on Computer Vision and Pattern Recognition (CVPR) Workshops, 2018, pp. 2156-2164.

Miller, C., "Apple execs talk Apple Watch, AirPods health and fitness monitoring, more in new interviews," [online] 9to5Mac, Jun. 16, 2021, retrieved from the Internet: <https://9to5mac.com/2021/06/16/apple-execs-apple-health-watch-watch-interview/>, 4 pg.

Golightly, D., "Google Patents Headphone-Based Health Monitoring Tech," [online] Copyright © 2021 Android Headlines, Sep. 21, 2018, retrieved from the Internet: <https://www.androidheadlines.com/2018/09/google-patents-headphone-based-health-monitoring-tech.html>, 3 pg.

* cited by examiner

| Movement | Discomfort Weight |
|---|---|
| Fast head turn to left | 0.5 |
| Slow head turn to left | 0.1 |
| Step 3 of Epley Maneuver | 0.2 |
| Cawthorne-Cooksey Exercises | 0.1 |
| Slow head turn to right | 0.1 |

410a

| Movement | Comfortable Completions |
|---|---|
| Fast head turn to left | 1/7 |
| Slow head turn to left | 5/5 |
| Step 3 of Epley Maneuver | N/A |
| Cawthorne-Cooksey Exercises | 3/5 |
| Slow head turn to right | 7/7 |

(Similarity between "Fast head turn to left" and "Step 3 of Epley Maneuver")

410b

| Movement | Discomfort Weight |
|---|---|
| Fast head turn to left | 0.55 |
| Slow head turn to left | 0.08 |
| Step 3 of Epley Maneuver | 0.22 |
| Cawthorne-Cooksey Exercises | 0.08 |
| Slow head turn to right | 0.07 |

Generate a sequence of sounds modulated to perceptually emanate from one or more distinct locations in 3D space relative to a user, the sequence predetermined to guide head movements of the user in a prescribed manner to mitigate vertigo experienced by the user
502

---

Track the head movements of the user as the user responds to the sequence of sounds
504

---

Convey a signal to the user in response to detecting a predetermined head movement of the user
506

FIG. 5

PERSONALIZED VERTIGO REHABILITATION

CROSS-REFERENCE TO RELATED APPLICATIONS

This application claims the benefit of U.S. Provisional Patent Application No. 63/271,535 filed on Oct. 25, 2021, which is incorporated herein by reference in its entirety.

TECHNICAL FIELD

This disclosure relates generally to monitoring and treating health conditions, and more particularly, to monitoring and treating vertigo.

BACKGROUND

Vertigo is characterized by extreme dizziness and is the sensation of spinning that a person experiences even though the person is not moving. The person may experience extreme discomfort and become disoriented. Vertigo can be mild or severe. With severe vertigo, the person may be unable to walk or maintain normal balance. Vertigo can develop suddenly. The symptoms of dizziness and feeling sick that typically accompany vertigo can last seconds or much longer, making it difficult for the person to engage in even routine activities. It is estimated that nearly 40 percent of the U.S. population has or will have experienced vertigo at least once. For some individuals, vertigo is a recurring condition.

SUMMARY

In an example implementation, a method can include generating with a device a sequence of sounds that are modulated to perceptually emanate from one or more distinct locations in three-dimensional space relative to a user of the device. The sequence can be predetermined to guide head movements of the user in a prescribed manner to mitigate vertigo experienced by the user. The method can include tracking head movements of the user with a device sensor as the user responds to the sequence of sounds. A signal can be conveyed to the user by the device, the signal conveyed to the user in response to detecting a predetermined head movement by the user.

In another example implementation, a system can include one or more processors. The one or more processors can be configured to initiate operations. The operations can include generating a sequence of sounds that are modulated to perceptually emanate from one or more distinct locations in three-dimensional space relative to a user. The sequence can be predetermined to guide head movements of the user in a prescribed manner to mitigate vertigo experienced by the user. The operations can include tracking head movements of the user as the user responds to the sequence of sounds. The operations can include conveying a signal to the user in response to detecting a predetermined head movement by the user.

In another example implementation, a computer program product includes one or more computer readable storage media, and program instructions collectively stored on the one or more computer readable storage media. The program instructions are executable by one or more processors of an electronic device to initiate operations. The operations can include generating a sequence of sounds that are modulated to perceptually emanate from one or more distinct locations in three-dimensional space relative to a user. The sequence can be predetermined to guide head movements of the user in a prescribed manner to mitigate vertigo experienced by the user. The operations can include tracking head movements of the user as the user responds to the sequence of sounds. The operations can include conveying a signal to the user in response to detecting a predetermined head movement by the user.

This Summary section is provided merely to introduce certain concepts and not to identify any key or essential features of the claimed subject matter. Other features of the inventive arrangements will be apparent from the accompanying drawings and from the following detailed description.

BRIEF DESCRIPTION OF THE DRAWINGS

The inventive arrangements are illustrated by way of example in the accompanying drawings. The drawings, however, should not be construed to be limiting of the inventive arrangements to only the particular implementations shown. Various aspects and advantages will become apparent upon review of the following detailed description and upon reference to the drawings.

FIGS. 4A-4C illustrate an example aspect of FIG. 1 for automatically learning which vertigo mitigation movements are likely to cause a user discomfort or which a user is unlikely to perform successfully.

FIG. 5 illustrates an example method of vertigo rehabilitation and treatment.

DETAILED DESCRIPTION

Figure 1:
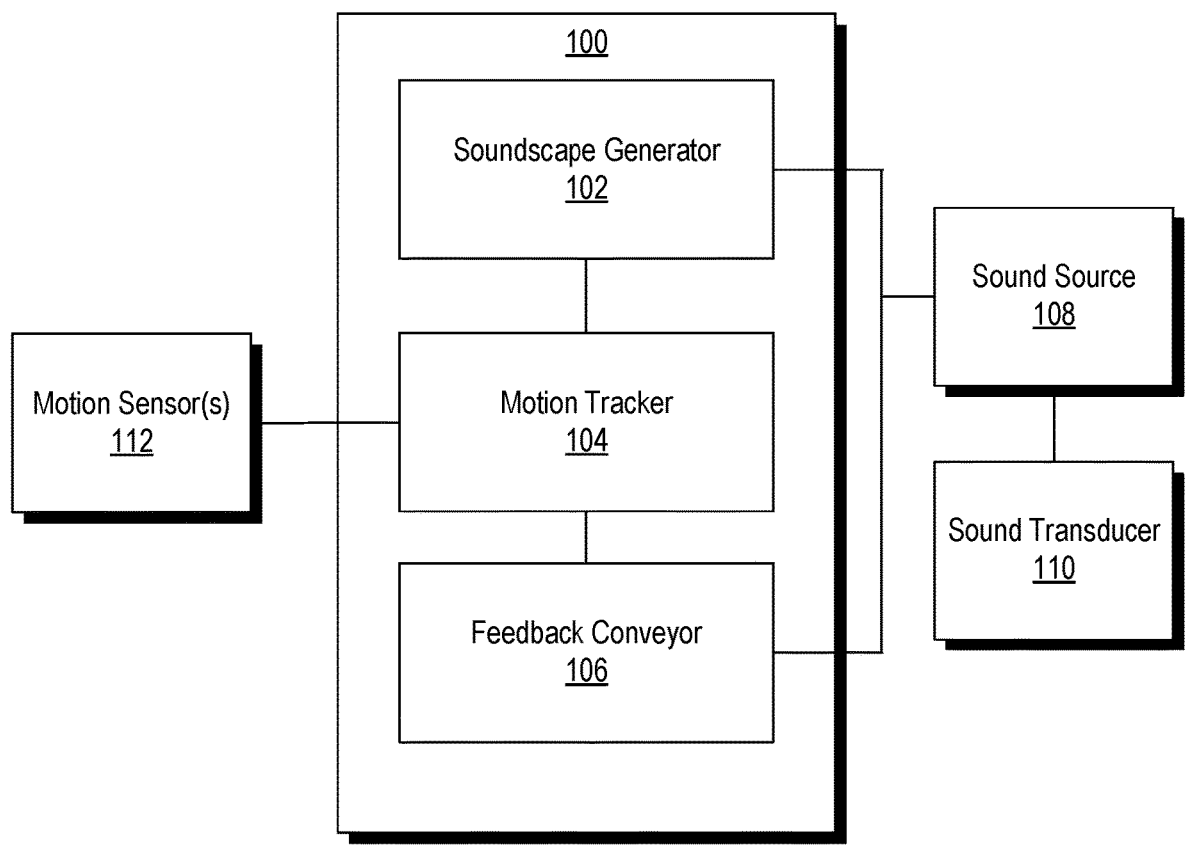
FIG. 1 illustrates an example vertigo rehabilitation and treatment system.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates generally to monitoring and treating health conditions, and more particularly, to monitoring and treating vertigo. Treatments for vertigo include having the afflicted individual undertake certain prescribed movements. Cawthorne-Cooksey exercises and the Epley maneuver, for example, are among the types of movements that physicians and other healthcare professionals at times recommend to individuals suffering from vertigo. There remain challenges, however, to relieving an on-going bout of vertigo or preventing future episodes using motion-based treatments. An individual may have to attempt—without professional guidance—different physical maneuvers and/or positions before achieving results. Without professional guidance, motion-based treatments may be ineffective. Motion-based treatment under professional guidance, however, can be costly both monetarily and in terms of time making and traveling to appointments with a professional. Moreover, tailoring movements to a specific individual to achieve the most effective results may be infeasible in many situations. It also may be impractical for a healthcare provider and patient to take full advantage of audio and visual aids for coaching the patient in performing the movements intended to treat the patient's vertigo.

In accordance with the inventive arrangements described within this disclosure, example methods, systems, and computer program products are capable of guiding a user through one or more prescribed head movements that can mitigate the user's vertigo. The movements can be machine-determined to accommodate specific hearing and/or other physical attributes of the user, and in this respect, are personalized for a specific user.

The arrangements disclosed herein are also capable of tracking the user's performance of the head movements, and based on the user's performance, provide feedback. In various arrangements, the feedback can be an audible signal and/or visual signal. The feedback can alert the user when the user performs a movement incorrectly. The feedback can encourage the user when the user performs the movement correctly. The feedback can provide verbal and/or visual guidance on how a movement is to be performed correctly. The tracking of the user's performance, in certain arrangements, can be the basis for a machine-generated report conveyed via a network connection to a healthcare provider.

In one aspect, the inventive arrangements leverage a portable device such as earbuds, smartphone, and the like for providing the various functions to the user. With such a device, the inventive arrangements provide the user with an easily accessible set of functions performed with the device to relieve bouts of vertigo and to gradually train the user's body to eliminate or minimize the effect of future episodes of vertigo. Implementation of the inventive arrangements in a portable device enables the user to perform vertigo treatment and rehabilitation from virtually any location and without direct supervision, obviating the need for frequent session with a physician or other healthcare provider. Nonetheless, inventive arrangements provide the user with a personalized approach to vertigo rehabilitation and treatment.

In one aspect, earbuds or other portable device are leveraged to create a soundscape around the user in which modulated sounds are perceived by the user as emanating from specific directions in a three-dimensional (3D) sound environment. The sounds presented within the soundscape can induce the user to perform head movements that effectively relieve the user's vertigo and minimize the likelihood of future episodes of vertigo. In another aspect, a system is disclosed that automatically learns to adjust stimuli and movement routines by detecting user discomfort and the user's inability to complete specific movements based on both electronically captured user data and machine-determined similarity between different movements. The captured user data and prior knowledge of similarity between movements enables an automated building of a personalized set of movements for mitigating vertigo experienced by the user.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

FIG. 1 illustrates an example vertigo rehabilitation and treatment system (system) 100. System 100 illustratively includes soundscape generator 102, motion tracker 104, and feedback conveyor 106. Operatively, soundscape generator 102 is capable of controlling sound source 108 (e.g., smartphone) to generate sounds that are conveyed via sound transducer 110 (e.g., earbuds) to a user. Through controlling sounds conveyed to the user, soundscape generator 102 creates a soundscape in which sounds can be perceived by the user as emanating from certain directions and can be perceived as moving from one location to another. Soundscape generator 102 modulates a sequence of sounds such that perceptually the sounds seem to the user to emanate from one or more distinct locations in a 3D space relative to the user. The sounds guide the user's head motion as the user responds to the sounds, for example, for example by turning to face the direction from which the sound is perceived to originate.

Motion tracker 104 is capable of tracking signals generated by one or more sensors 112. In one or more examples, sensor(s) 112 may include Inertial Measurement Units (IMUs) that may be included in one or more wearable devices. Example of wearable devices include those worn on the user's head and may include, but are not limited to, smart eyeglasses, earbuds, other varieties of headphones, and the like. Sensor(s) 112 are capable of determining the turning and positioning of the user's head. For example, in some arrangements, sensor(s) 112 implemented as earbud IMUs are capable of generating signals in response to the user's head movement. As the user's head moves in response to the signals generated by soundscape generator 102, and the IMUs generate motion-based signals in response to the head movement, motion tracker 104 detects the signals and tracks the user's head movement. The sounds created by soundscape generator 102 are predetermined to induce head motions according to a prescribed manner. The prescribed head motions are ones that can mitigate vertigo currently experienced by the user and/or reduce or eliminate future occurrences of vertigo. Motion tracker 104 tracks the user's head motions to determine whether the motions are performed in accordance with the motions prescribed.

Feedback conveyor 106 is capable of providing feedback to the user in response to the head motions performed by the user. The feedback can encourage the user to continue the same movements and/or can suggest one or more corrective changes in movement, depending on the how closely the user's head movement corresponds to those prescribed. Audible feedback (e.g., instructive correction, guidance, encouragement) can be conveyed to the user through sound transducer 110 or other user-interface of the device in which system 100 is integrated or operatively coupled with.

In certain embodiments, system 100 electronically stores data corresponding to one or more prescribed head movements to mitigate the user's vertigo. Motion tracker 104 can generate data derived from signals generated by one or more sensors in response to a user's head movement. System 100 can include a comparator such as movement comparator 400 (FIGS. 4A-C) that compares the sensor-generated data with electronically stored data corresponding to one or more prescribed head movements and based on the comparison determines a predetermined head movement. The predetermined head movement can be a non-prescribed head movement, namely one that deviates from any prescribed head movement or one that conforms to a prescribed head movement. Feedback conveyor 106, depending on the predetermined head movement, can respond accordingly. Feedback conveyor 106, for example, can convey a signal that provides a user notification and/or an instruction or other guidance on how the movement should be performed if the predetermined movement deviates from a prescribed one. Alternatively, feedback conveyor 106 can convey a signal that provides encouragement (e.g., pre-recorded audible message) to the user in response to a predetermined head movement that conforms to a prescribed head movement.

Figure 6:
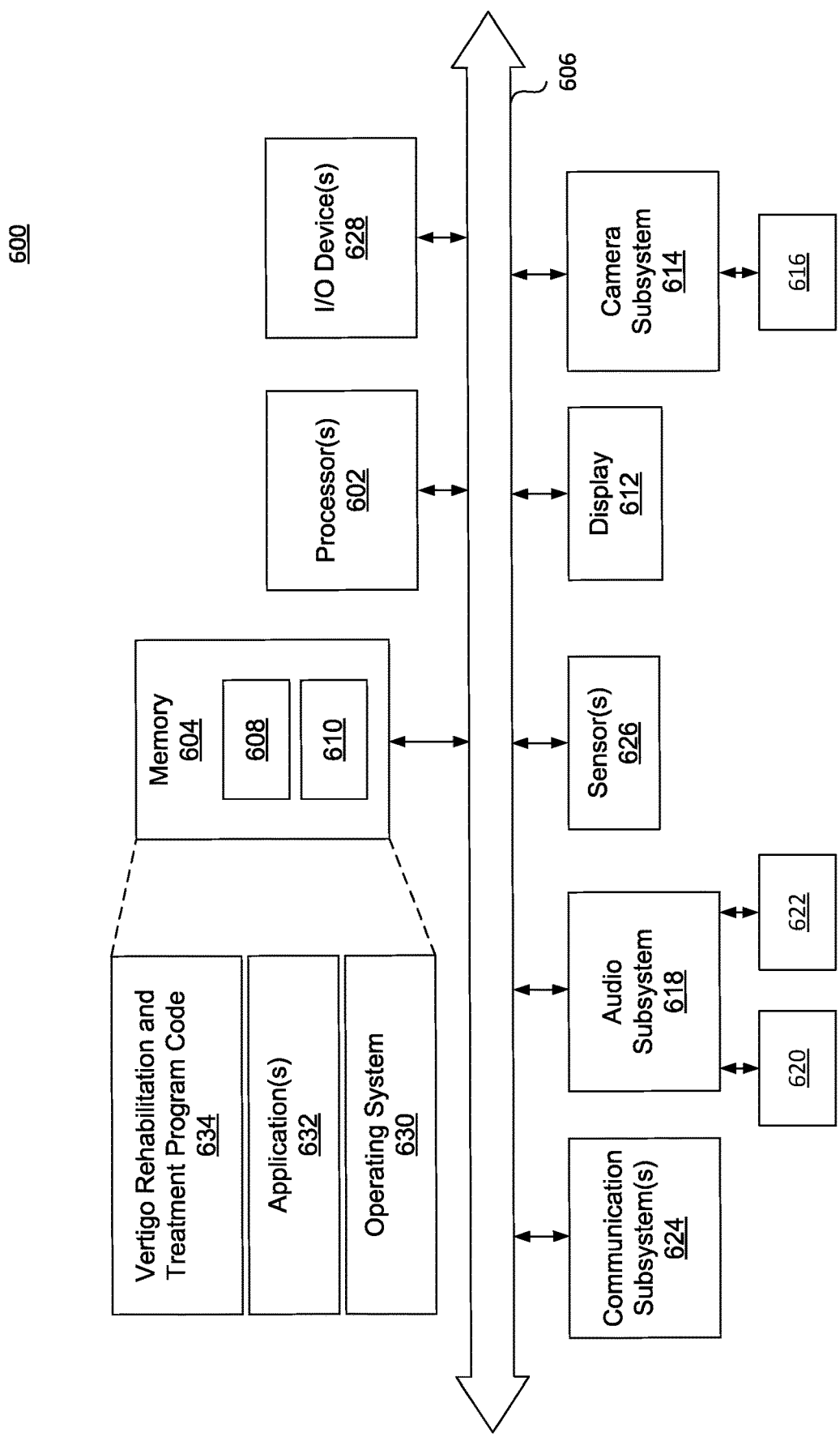
FIG. 6 illustrates an example device for implementing the system of FIG. 1.

In various embodiments, each of the illustrative components of system 100 can be implemented in hardware (e.g., dedicated hardwired circuitry), software (e.g., program code executed by one or more processors), or a combination thereof. System 100 can be integrated in, or operatively coupled with, an electronic device such as device 600 (FIG. 6). For example, implemented in a device such as device 600, the components of system 100 can comprise program code that is electronically stored in a memory, such as memory 604, and executes on one or more processors, such as processor(s) 602 (FIG. 6).

System 100 in some arrangements is implemented in a first device that operatively couples with a second device. For example, sound source 108 can comprise a smartphone in which system 100 is implemented in software running on the smartphone. Sound transducer 110 can comprise a pair of earbuds that connect via a wireless (e.g., Bluetooth) or wired connection with the portable device. In other arrangements, sound source 108 and sound transducer 110 can be integrated within a head-mounted device (HMD), with system 100 implemented in software running on a console, computing-enabled appliance or consumer electronic device, or data processing system that communicatively couples with the HMD. In some arrangements, system 100 can be wholly implemented in the HMD itself, the HMD containing hardwired circuitry and/or software processing capabilities for performing the functions of system 100.

Figure 2:
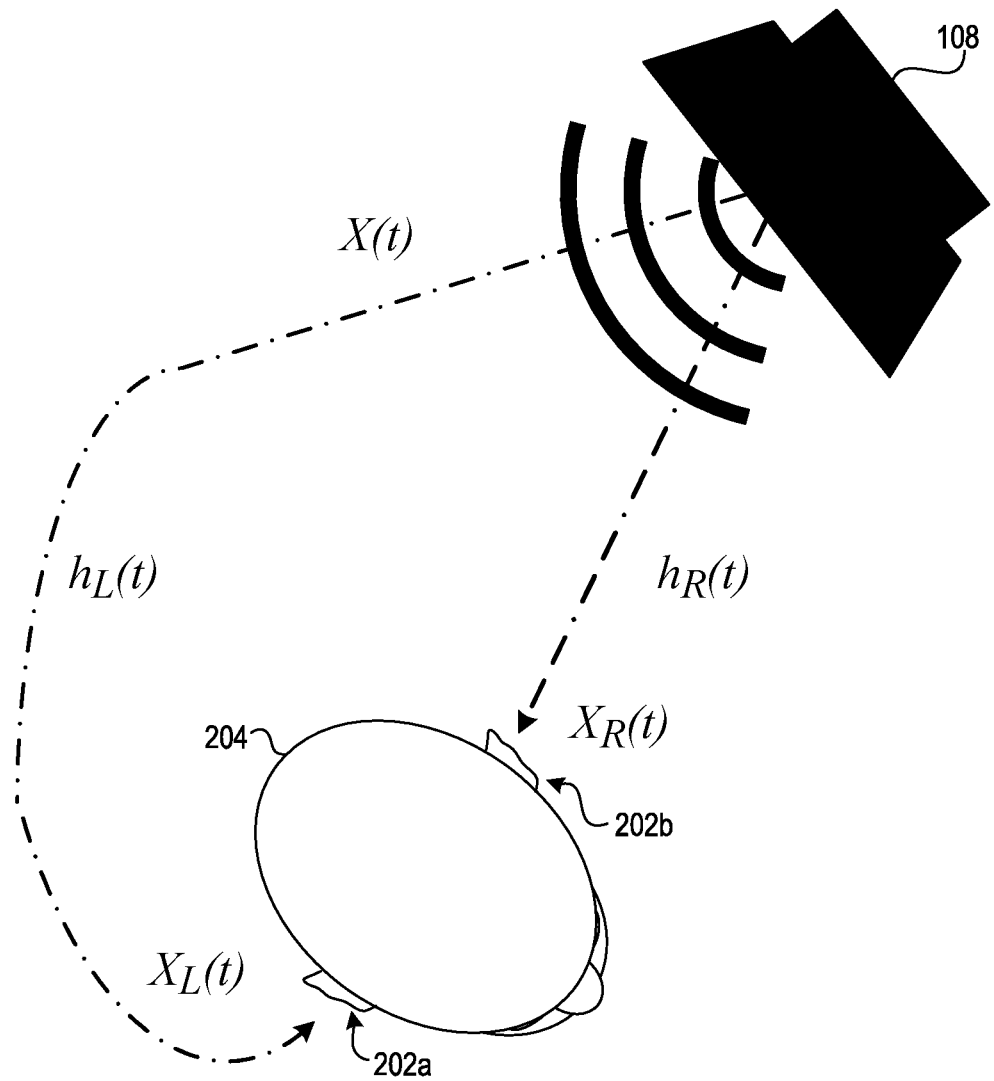
FIG. 2 schematically illustrates an example procedure for calibrating a component of the system of FIG. 1.

Referring additionally to FIG. 2, an example calibration procedure 200 for calibrating soundscape generator 102 is schematically illustrated. In accordance with calibration procedure 200, sounds X(t) emanating from sound source 108 are repeated with gradually increasing volume in left and right channels corresponding, respectively, to left earbud 202a and right earbud 202b. By gradually increasing volume in the left and right channels, calibration procedure 200 can accurately, and independently, measure the hearing in each ear of user 204. Volume in each channel can be incrementally increased until user 204 responds with head movement. For example, an initial volume 40 decibels (sound level of whisper) can be gradually increased by 5 decibels until the user responds. Calibration procedure 200 establishes head-related transfer function (HRTF), $h(t)_L$, for the left channel and HRTF, $h(t)_R$, for the right channel. Accordingly, soundscape generator 102 generates a sound intensity $h(t)_L \cdot (t)=X(t)_L$ via the left channel and a sound intensity $h(t)_R \cdot X(t)=X(t)_R$ via the right channel.

The separate and independent determination of a specific HRTF for each channel takes into account any variation in hearing capability of the user in one ear versus the other. The HRTF determined according to the hearing in each ear of the user enables the rendering of sounds that the user perceives as emanating in 3D space. Accordingly, soundscape generator 102 is capable of generating a soundscape that, based on the user-specific calibration of soundscape generator 102, provides balanced binaural hearing that can account for possibly different hearing capacity with the user's different ears. This can be an important factor given that hearing loss is a significant comorbidity of individuals afflicted with recurrent vertigo.

Figure 3:
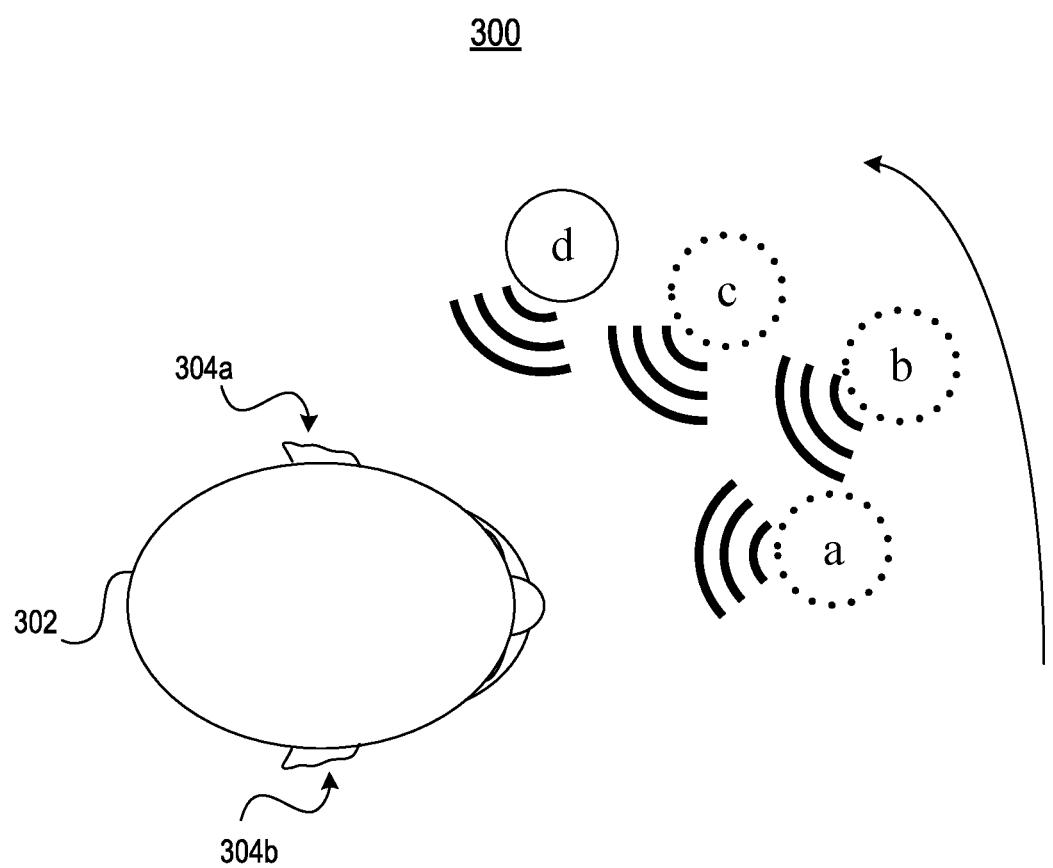
FIG. 3 schematically illustrates example sound modulation simulating movement using the system of FIG. 1.

The HRTF, specific to a user, is calibrated with respect to differences in hearing capacity of each ear of the user. Based on the HRTF, soundscape generator 102 can change the intensity of sounds, can modulate the frequencies of sounds, and/or present different types of sounds heard by the user in each ear. For example, soundscape generator 102 uses the HRTF in controlling the speed with which sounds in the 3D space are perceived to be moving by the user. Referring additionally now to FIG. 3, sound modulation by soundscape generator 102 for simulating example sound movement 300 is schematically illustrated. By varying the sound intensity between the left and right channels, while accounting for the user's hearing differences, soundscape generator 102 can cause the user to perceive sound movement 300 in which sounds seem to emanate from shifting locations. Illustratively, given an initial sound intensity, user 302 perceives sound as emanating from location a through locations b and c, and finally location d. Soundscape generator 102 can create the effect by varying the intensity of the sound through each channel. Initially, the sound user 302 hears in earbuds 304a and 304b is initially balanced but begins to fade in the left ear and increase in the right until, as perceived by user 302, the sound smoothly completes an arc-like movement.

The smooth, arc-like movement that user 302 perceives the sound source as making can cause user 302 to respond with a similarly smooth movement of the head—from facing center to facing to user 302's left. If the sound traverses the arc relatively slowing and user 302's head moves at a commensurate speed, the head movement is also smooth. This avoids a swift jerk of user 302's head. Such jerking motions, rather than ameliorating vertigo, can exacerbate the sensation. Even if a user is not currently experiencing vertigo, a swift jerk of the user's head can bring on vertigo. The user-specific HRTF, calibrated as described above, enables soundscape generator 102 to create sounds that can cause a smooth measured movement of the user's head, as opposed to a swift jerking motion.

Soundscape generator 102 generates a sequence of sounds that are predetermined to guide the head movements of the user in a prescribed manner. The prescribed head movements can be specific to the user so as to mitigate the vertigo experienced by the user. Still referring to FIG. 1, motion tracker 104 based on signals generated by sensor(s) 112 can determine whether the user is performing the head movements correctly. Feedback conveyor 106 provides feedback in response to the user's motion tracked by motion tracker 104. In certain arrangements, feedback conveyor 106 conveys a signal to the user indicating that the user's movement deviates from a prescribed movement. Optionally, motion tracker 104 can detect a deviation that exceeds a predetermined threshold and, in response, prompt feedback conveyor 106 to convey feedback alerting the user. For example, soundscape generator 102 can generate a sequence of sounds that emulates a gradual movement from one of the one or more locations to another of the one or more locations, the gradual movement calibrated to guide the head movement of the user at a pace likely to avoid inducing or exacerbating the vertigo. Motion tracker 104 can determine that the user's pace is too rapid, and in response, feedback conveyor 106 can provide feedback to cause the user to slow the pace of movement.

In some arrangements, the feedback can be an audible signal conveyed to the user, for example, via sound transducer 110 (e.g., earbuds). In other arrangements described in greater detail below, the feedback can be visual. Feedback can include, for example, a corrective instruction pre-recorded and annotated to play in response to motion tracker 104 detecting a specific deviation from a prescribed movement. Feedback can include, for example, a pre-recorded encouragement that is conveyed in response to motion tracker 104 detecting that the user successfully performed a prescribed movement. In certain embodiments described in greater detail below feedback can be conveyed via a display operatively coupled with system 100, wherein in a video is displayed that instructs the user in the proper manner of performing a prescribed movement.

System 100, in some embodiments performs noise cancellation to cancel ambient sounds. The noise cancellation can be performed by system 100 in response to determining that the measure of loudness of the ambient sounds is likely to impede the user's hearing the sequence of sounds intended to guide the user's head movement and/or the signal conveyed to the user in response to monitoring the user's head movement.

Head movements are ineffective in treating a user's vertigo if the user is unable or reluctant to perform the head movements correctly. Accordingly, in certain arrangements, motion tracker 104 is capable of identifying a particular movement or class of movements that cause the user discomfort or that the user in incapable of performing.

Figure 4A:
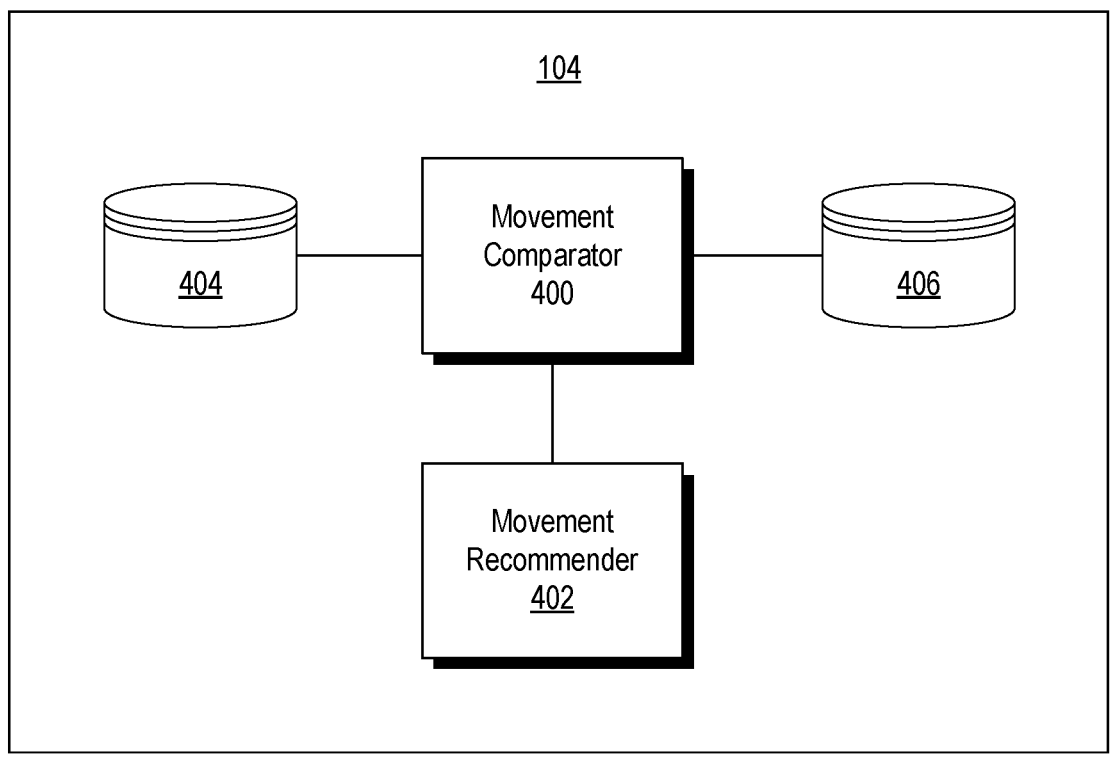
Figure 4B:
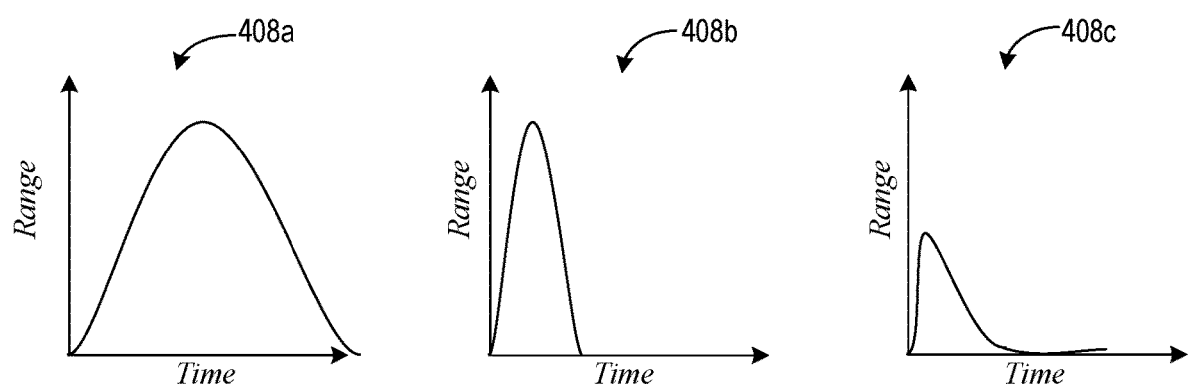

FIGS. 4A-4C illustrate an example embodiment and certain operations of motion tracker 104 that automatically learns which movements, if any, likely cause the user discomfort or that the user is incapable of performing. Motion tracker 104, as shown in FIG. 4A, illustratively includes movement comparator 400 and movement recommender 402, as well as user movement database 404 and prior knowledge database 406. Operatively, motion tracker 104 records and electronically stores in user movement database 404 movements of the user that are sensed by sensor(s) 112. Motion tracker 104 can determine the user's difficulty with respect to a particular movement based, for example, on two criteria—namely, time-of-completion and extent-of-completion. The first criterion, time-of-completion, indicates that a user struggles with a specific movement if the user fails to complete the movement within a predetermined time. The second criterion, extent-of-completion, indicates that the user is unable to complete a predetermined portion of the full range of motion of a prescribed movement within a certain number of attempts.

Movement comparator 400 retrieves data from user movement database 404, which electronically stores data detailing one or more of the user's attempted movements as sensed by sensor(s) 112. For comparison, movement comparator 400 retrieves a template of the same or similar movement from prior knowledge database 406. FIG. 4B illustrates the determination of at least one of the criteria based on a comparison of the user's attempt to perform a specific motion, which movement comparator 400 compares with a template of the same or a similar movement. Plot 408a depicts an example plot of the user's motion based on sensor-generated data. Plot 408b depicts an example plot of an ideal time for completing a full range of motion performing the same or similar movement. Comparison of plot 408a of the user's movement with plot 408b reveals that the user took longer than a predetermined time to complete the movement. Movement comparator 400, for example, can determine the user failed to successfully complete a movement within a specified time threshold (e.g., 50 percent longer than the ideal time of completion). Plot 408c depicts an example plot of a user movement that is incomplete. By comparison with ideal plot 408b, example plot 408c reveals that the user failed to complete the full range of the movement. Movement comparator 400 can determine the user failed to successfully complete a sufficient portion of the full range of movement within a specified number of attempts (e.g., less than 80 percent of the full range after five failed attempts).

Based on a movement that the user has attempted and failed to complete according to either of the above-described criteria, movement comparator 400 can determine whether another movement the user has not attempted is also likely to cause the user discomfort or is impossible for the user to fully complete. Movement comparator 400, in certain embodiments, implements a Causal Bayesian Network (CBN) to predict movements likely to cause the user discomfort or that the user is unlikely to complete. The CBN is a probabilistic graphical model, aspects of which include reducing the number of parameters needed for defining a posterior probability distribution. Using the CBN, movement comparator 400 automatically learns a posterior probability distribution based on which movement comparator 400 determines specific movements that are likely to cause the user discomfort or that the user is unlikely to completely perform successfully.

Movement comparator 400 can update the CBN by establishing similarity links between prescribed movements for mitigating vertigo—data for which are electronically stored in prior knowledge database 406—and movements that are likely to cause the user discomfort or that the user is unlikely to completely perform successfully. In certain embodiments, movement comparator 400 implements dynamic time warping (DTW). DTW is an algorithmic process for determining a match between two sequences of sequential data, which in the instant context comprises a succession of body motions in completing the full range of a given movement (e.g., head turn). A match determined by DTW is one that meets certain constraints with a minimal cost, which is computed as the sum of differences between the two sequences. Movement comparator 400 can determine whether a prescribed movement is likely to cause the user discomfort or is impossible for the user to complete even if the user has not ever attempted the movement. The determination is based on movement comparator 400 determining, based on a computed DTW distance, that the prescribed movement has a strong similarity link with a movement that the user has attempted and failed to complete according to either of the above-described criteria.

FIG. 4C illustrates the use of the CBN and DTW in the context monitoring certain user movements by motion tracker 104, the monitoring enabling movement recommender 402 to generate a recommendation that identifies movements that the user is likely capable of performing successfully without discomfort. In certain embodiments, motion tracker 104 monitors a predetermined set of user movements. The movements can comprise, for example, (1) a fast head turn to the left; (2) a slow head turn to the left; (3) the third step of the Epley maneuver; (4) the Cawthorne-Cooksey exercises; and (5) a slow head turn to the right. Each movement can be assigned a discomfort weight, as illustrated by table 410a. The initial discomfort weights can be provided by data drawn from a sample of a relevant population who share with the user similar characteristics and electronically stored in prior knowledge database 406. The discomfort weights can be periodically updated (e.g., weekly) based on sensor-generated data collected by motion tracker 104 and electronically stored in user movement database 404. The updating can reflect, for example, physiological changes that the user may experience over time that affect the user's ability to perform the movements without discomfort. The second column of table 410b depicts the number of comfortable completions of each movement. Table 410c illustrates the updating of the discomfort weights based on the data. Illustratively, the user never attempted step three of the Epley maneuver, and only once successfully completed a fast head turn to the left after seven attempts. The discomfort weight assigned to a fast head turn to the left is increased accordingly, but no data is available for step three of the Epley maneuver. Nonetheless, based on a DTW score between the fast head turn to the left and step three of the Epley maneuver, movement comparator 400 establish a similarity link between the two movements and, accordingly, assigns a score to step three of the Epley maneuver notwithstanding that the user never attempted the movement.

Based on the updated results, movement recommender 402 generates a recommendation that of the five monitored movements, the user only perform the second, fourth, and fifth unless and until the discomfort weights are revised. The recommendation can be conveyed to the user via an interface of the device in which system 100 is implemented and/or, for example, to the user's physician (e.g., via an Internet connection or other communications channel). Optionally, system 100 can compile and electronically store an indicator corresponding to exercises determined to cause the user discomfort or that the user is incapable of fully performing successfully. System 100, accordingly, can restrict generation of sounds by soundscape generator 102 that, based on prior knowledge, are likely to induce the user to attempt the movements determined to cause the user discomfort or that the user is incapable of fully performing successfully.

In some embodiments, sensor(s) 112 can include other sensors, such as a photoplethysmography (PPG) sensor, which provide data pertaining to certain physical attributes of the user. For example, system 100 can be implemented in, or operatively coupled with, a pair of earbuds, which include a sensor such as a PPG sensor. The PPG sensor can, for example, measure the user's blood pressure, heart rate, and other physical attributes. Using data generated by a PPG or other health-monitoring sensor, for example, system 100 can monitor the user's stress level during performing the movements to identify certain confounding factors (e.g., high blood pressure) that can affect the user's performance of vertigo-mitigating movements or adversely affect the user. For example, system 100 can compile and electronically store an indicator corresponding to exercises that are correlated with a predetermined rise in the user's heart rate and/or blood pressure. System 100, as a result, can restrict generation of sounds by soundscape generator 102 that, based on prior knowledge, are likely to induce the user to attempt the movements correlated with an adverse physical reaction (e.g., elevated heart rate or blood pressure) in the user.

In certain embodiments, system 100 is implemented in a device that includes, or is operatively coupled with, a camera system such as camera subsystem 614 and an audio subsystem such as audio subsystem 618 (FIG. 6). The camera subsystem can include one or more motion-tracking cameras, and the audio subsystem can include a surround-sound speaker arrangement of multiple speakers. The motion-tracking cameras can be operatively coupled with motion tracker 104 for monitoring head movements of the user as the user responds to a sequence of sounds generated by soundscape generator 102 as the sounds are modulated to perceptually emanate from one or more distinct locations in 3D space relative to the user of the device. Feedback conveyor 106 can convey audio and/or visual feedback via a device display and/or sound transducer, the feedback conveyed to the user in response to the user's monitored movements for correcting and/or encouraging the user's movements.

In some embodiments, system 100 can be implemented in, or operatively coupled with, a device such as an extended-reality (XR) console and headset or an HMD. The XR headset or HMD can be endowed with circuitry and/or software for head-motion tracking and gaze tracking. Soundscape generator 102 can be augmented with a capacity to generate visual clues—with or without audible sounds—that are presented visually using the XR headset or HMD. The visual cues, alone or in conjunction with a sequence of audible cues, can be selected to guide the user to perform certain movements that mitigate the user's vertigo. In some arrangements, the visual cues comprise augmented reality (AR) objects interposed within the user's field of view. The user can be prompted to undertake certain body motions as the user engages in simulated interactions with the AR objects. Motion tracker 104 can track the user's movements, and feedback conveyor 106 can convey one or more signals via the XR headset in response to the user's movements.

In still other embodiments, system 100 can be implemented in a device that includes a communication subsystem such as communication subsystem 624 (FIG. 6) with which the device wirelessly, or via a wired connection, connects with a communication network (e.g., the Internet). In certain arrangements, the device connects to a network site maintained by a physician or other healthcare provider that treats the user's vertigo. System 100 is thus capable of providing a communication channel through which the user interacts remotely with the healthcare provider. For example, in some arrangements, motion tracker 104 can track movements prescribed by the healthcare provider and conveyed to the user via the communication network. Movement comparator 400 can determine whether the user is performing the prescribed movements correctly. Feedback conveyor 106 can convey one or more signals (audio and/or visual) to correct incorrect movements by the user. Movement recommender 402 can receive additional input from the user (e.g., verbal input) indicating whether the prescribed movements in fact mitigate the vertigo experienced by the user. In certain embodiments, movement recommender 402 can generate a report characterizing the user's performance (e.g., number of fully completed movements as prescribed) and/or the user's self-assessment of whether the movements mitigate the user's vertigo. In some arrangements, the report can include images and/or video that record the user performing the prescribed movements. System 100 can convey the report to the healthcare provider via the communication network. As needed, the healthcare provider can respond via the communication network with additional guidance to the user. In some embodiments, system 100 establishes a real-time audio and/or audio-visual link with the remotely located healthcare provider. The link enables the user and healthcare provider to interact audibly and/or visually in real-time as the user undertakes various movements to mitigate the user's vertigo FIG. 5 illustrates an example method of vertigo rehabilitation and treatment (method) 500. Method 900 may be performed by one or more electronic devices that includes a system such as system 100 as described herein. The electronic device(s) and system integrated therein or operatively coupled therewith are, collectively, "the system" that performs method 900.

At block 502, a sound source of one of the one or more electronic devices of the system generates a sequence of sounds that are modulated to perceptually emanate from one or more distinct locations in a 3D space relative to a user. The sequence is predetermined to guide head movements of the user in a prescribed manner to mitigate vertigo experienced by the user. At block 504, one or more sensors of the same or a second electronic device of the system tracks the head movements of the user as the user responds to the sequence of sounds.

At block 506, the system conveys a signal to the user in response to detecting one or more predetermined head movements of the user. The signal can be conveyed via the same or the second or a third electronic device of the system. The signal can be an audio signal and/or a visual signal. The one or more predetermined head movements can include, for example, a head movement that the user fails to perform as prescribed, and the signal conveyed can indicate the failure. Optionally, the signal can provide an instruction or other guidance on how the movement should be performed. The one or more predetermined head movements, for example, can include a head movement that, in fact, the user performs fully and correctly as prescribed, to which the signal conveyed provides positive enforcement such as an audible signal voicing a pre-recorded message of encouragement.

In certain embodiments, the system generates the sequence of sounds based on a user-specific head-related transfer function calibrated in response to detecting a binaural hearing capability of the user. The sequence of sounds can emulate a gradual movement from one location to another, the gradual movement calibrated to guide the head movement of the user at a pace likely to avoid inducing or exacerbating the vertigo.

The system, based on the tracking, can determine a pace of the head movement of the user. The system can convey one or more signals providing guidance based on a comparison of the pace with a predetermined threshold.

In other embodiments, the system uses noise cancellation to cancel ambient sounds. The noise cancellation is performed by the system in response to determining that the measure of loudness of the ambient sounds is likely to impede the user's hearing the sequence of sounds or the signal conveyed in response to monitoring the user's movement.

In still other embodiments, the system identifies a problematic head movement likely to cause the user discomfort or that the user is unlikely to complete successfully. The identification can be based on the system detecting that the user failed to perform the problematic head movement within a predetermined time or that the user failed to complete a predetermined portion of a full range of the problematic head movement after a predetermined number of attempts. The system can identify a second head movement likely to cause the user discomfort or that user is unlikely to complete successfully, the identifying based on determining a similarity link between the problematic head movement and the second head movement using automated learning. The determination of a similarity link can be made using a machine-learning model that learns to identify similarities between different body movements.

In yet other embodiments, the system can display one or more XR objects using a display of the electronic device. The system can cause the XR objects to appear to move in a predetermined manner that causes the user to respond in a prescribed manner so as to mitigate the vertigo experienced by the user.

In some embodiments, the system generates a report. The report can be based on the tracking by the system of the user's performing movements prescribed to mitigate the user's vertigo. The system can convey the report via a communication network to a predetermined healthcare provider. Feedback from the healthcare provider can be conveyed to the user via the communication network.

FIG. 6 illustrates an example device 600 in which system 100 can be implemented. Device 600 includes one or more processors 602 coupled to memory 604 through interface circuitry 606. Device 600 stores computer readable instructions (also referred to as "program code") within memory 604, which is an example of computer readable storage media. Processor(s) 602 execute the program code accessed from memory 604 via interface circuitry 606.

Memory 604 can include one or more physical memory devices such as local memory 608 and bulk storage device 610, for example. Local memory 608 is implemented as one or more non-persistent memory device(s) generally used during actual execution of the program code. Local memory 608 is an example of a runtime memory. Examples of local memory 608 include any of the various types of random-access memory (RAM) suitable for use by a processor for executing program code. Bulk storage device 610 is implemented as a persistent data storage device. Examples of bulk storage device 610 include a hard disk drive (HDD), a solid-state drive (SSD), flash memory, a read-only memory (ROM), an erasable programmable read-only memory (EPROM), electrically erasable programmable read-only memory (EEPROM), or other suitable memory. Device 600 can also include one or more cache memories (not shown) that provide temporary storage of at least some program code to thereby reduce the number of times program code must be retrieved from a bulk storage device during execution.

Examples of interface circuitry 606 include, but are not limited to, an input/output (I/O) subsystem, an I/O interface, a bus system, and a memory interface. For example, interface circuitry 606 can be implemented as any of a variety of bus structures and/or combinations of bus structures including a memory bus or memory controller, a peripheral bus, an accelerated graphics port, and a processor or local bus.

In one or more example implementations, processor(s) 602, memory 604, and/or interface circuitry 606 are implemented as separate components. Processor(s) 602, memory 604, and/or interface circuitry 606 may be integrated in one or more integrated circuits. The various components in device 600, for example, can be coupled by one or more communication buses or signal lines (e.g., interconnects and/or wires). Memory 604 may be coupled to interface circuitry 606 via a memory interface, such as a memory controller or other memory interface (not shown).

Device 600 can include one or more displays. Illustratively, for example, device 600 includes display 612 (e.g., a screen). Display 612 can be implemented as a touch-sensitive or touchscreen display capable of receiving touch input from a user. A touch sensitive display and/or a touch-sensitive pad is capable of detecting contact, movement, gestures, and breaks in contact using any of a variety of avail, able touch sensitivity technologies. Example touch sensitive technologies include, but are not limited to, capacitive, resistive, infrared, and surface acoustic wave technologies, and other proximity sensor arrays or other elements for determining one or more points of contact with a touch sensitive display and/or device.

Device 600 can include camera subsystem 614. Camera subsystem 614 can be coupled to interface circuitry 606 directly or through a suitable input/output (I/O) controller. In certain embodiments, camera subsystem 614 can include one or more motion-tracking cameras. The motion-tracking camera(s), in certain arrangements, can operatively couple with audio subsystem 618 (below), which can include a surround-sound speaker arrangement of multiple speakers. The operatively coupled motion-tracking cameras and surround-sound speaker arrangement for monitoring the movements of the user as the user responds to a sequence of sounds select to guide the user's movements to mitigate vertigo, as described above.

Camera subsystem 614 can be coupled to optical sensor 616. Optical sensor 616 can be implemented using any of a variety of technologies. Examples of optical sensor 616 can include, but are not limited to, a charged coupled device (CCD) or a complementary metal-oxide semiconductor (CMOS) optical sensor. Optical sensor 616, for example, can be a depth sensor. Camera subsystem 614 and optical sensor 616 are capable of performing camera functions such as recording or capturing images and/or recording video.

Device 600 can include an audio subsystem 618. Audio subsystem 618 can be coupled to interface circuitry 606 directly or through a suitable input/output (I/O) controller. Audio subsystem 618 can be coupled to a speaker 620 and a microphone 622 to facilitate voice-enabled functions, such as voice recognition, voice replication, digital recording, and telephony functions.

Device 600 can include one or more communication subsystems 624, each of which can be coupled to interface circuitry 606 directly or through a suitable I/O controller (not shown). Each of communication subsystem(s) 624 is capable of facilitating communication functions. The communication functions can include connecting wirelessly or via wired connection to a data communication network (e.g., the Internet). Communication subsystems 624 can include, for example, one or more wireless communication subsystems such as, but are not limited to, radio frequency receivers and transmitters, and optical (e.g., infrared) receivers and transmitters. The specific design and implementation of communication subsystem 624 can depend on the particular type of device 600 implemented and/or the communication network(s) over which device 600 is intended to operate.

As an illustrative and non-limiting example of a wireless communication system, communication subsystem(s) 624 can be designed to operate over one or more mobile networks, WiFi networks, short range wireless networks (e.g., a Bluetooth), and/or any combination of the foregoing. Communication subsystem(s) 624 can implement hosting protocols such that device 600 can be configured as a base station for other devices.

Device 600 may include one or more sensors 626 of various types, each of which can be coupled to interface circuitry 606 directly or through a suitable I/O controller (not shown). Sensor(s) 626 can include ones especially suited for detecting and/or measuring physiological attributes of the user such as the user's blood pressure, heart rate, or other physical attribute. For example, sensor(s) 626 can include a PPG sensor. The PPG sensor uses a light source and photodetector to measure the volumetric variations of the user's blood circulation. Accordingly, if device 600 for example is an earbud in which the PPG sensor is integrated, the PPG sensor can estimate skin blood flow of the user by emitting and detecting reflected infrared light in the user's ear canal. Device 600, in other embodiments, can be another type of wearable device (e.g., smartwatch) having a PPG sensor or can be a device such as a smartphone having a PPG sensor. The PPG sensor can measure heart rate, blood pressure, oxygen saturation, and other physiological attributes. Sensor(s) 626 can include an IMU to detect motion of the user. Device 600 can be a smartwatch, earbuds, or other wearable device in which an IMU is integrated. Device 600, in other embodiments, can be a smartphone or other such device in which an IMU is integrated.

Other examples of sensor(s) 626 that can be included in device 600 include, but are not limited to, a proximity sensor to facilitate orientation, lighting, and proximity functions, respectively, of device 600. Still other examples of sensors 626 can include, but are not limited to, a location sensor (e.g., a GPS receiver and/or processor) capable of providing geo-positioning sensor data, an electronic magnetometer (e.g., an integrated circuit chip) capable of providing sensor data that can be used to determine the direction of magnetic North for purposes of directional navigation, an accelerometer capable of providing data indicating change of speed and direction of movement of device 600 in 3D, and an altimeter (e.g., an integrated circuit) capable of providing data indicating altitude.

Device 600 further may include one or more input/output (I/O) devices 628 coupled to interface circuitry 606. I/O device(s) 628 can be coupled to interface circuitry 606 either directly or through intervening I/O controllers (not shown). Examples of I/O devices 628 include, but are not limited to, a track pad, a keyboard, a display device, a pointing device, one or more communication ports (e.g., Universal Serial Bus (USB) ports), a network adapter, and buttons or other physical controls. A network adapter refers to circuitry that enables device 600 to become coupled to other systems, computer systems, remote printers, and/or remote storage devices through intervening private or public networks. Modems, cable modems, Ethernet interfaces, and wireless transceivers not part of wireless communication subsystem(s) 624 are examples of different types of network adapters that may be used with device 600. One or more of I/O devices 628 may be adapted to control functions of one or more or all of sensors 626 and/or one or more of wireless communication subsystem(s) 624.

Memory 604 stores program code. Examples of program code include, but are not limited to, routines, programs, objects, components, logic, and other data structures. For purposes of illustration, memory 604 stores an operating system 630 and application(s) 632. In addition, memory 604 can store vertigo rehabilitation and treatment program code 634 for implementing a system, such as system 100.

Device 600 is provided for purposes of illustration and not limitation. A device and/or system configured to perform the operations described herein can have a different architecture than illustrated in FIG. 6. The architecture can be a simplified version of the architecture described in connection with FIG. 6 that includes a memory capable of storing instructions and a processor capable of executing instructions. In this regard, device 600 may include fewer components than shown or additional components not illustrated in FIG. 6 depending upon the particular type of device that is implemented. In addition, the particular operating system and/or application(s) included can vary according to device type as can the types of I/O devices included. Further, one or more of the illustrative components can be incorporated into, or otherwise form a portion of, another component. For example, a processor may include at least some memory.

Device 600 can be implemented as a data processing system, a communication device, or other suitable system that is suitable for storing and/or executing program code. Device 600 can be implemented as an edge device. Example implementations of device 600 can include, but are not to limited to, computing devices. Computing devices include, for example, a computer (e.g., desktop, laptop, tablet computer), a television, an entertainment console, an XR system, or other appliance capable of cooperatively operating as a display device (e.g., HMD, AR glasses) or a source device (e.g., smartphone, console, computer) operating in conjunction with an electronic display device, as described herein.

The terminology used herein is for the purpose of describing particular embodiments only and is not intended to be limiting. Notwithstanding, several definitions that apply throughout this document now will be presented.

As defined herein, the singular forms "a," "an," and "the" are intended to include the plural forms as well, unless the context clearly indicates otherwise.

The term "approximately" means nearly correct or exact, close in value or amount but not precise. For example, the term "approximately" may mean that the recited characteristic, parameter, or value is within a predetermined amount of the exact characteristic, parameter, or value.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without human intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. The different types of memory, as described herein, are examples of a computer readable storage media. A non-exhaustive list of more specific examples of a computer readable storage medium may include: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, or the like.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the term "processor" means at least one hardware circuit. The hardware circuit may be configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "responsive to" and similar language as described above, e.g., "if," "when," or "upon," mean responding or reacting readily to an action or event. The response or reaction is performed automatically. Thus, if a second action is performed "responsive to" a first action, there is a causal relationship between an occurrence of the first action and an occurrence of the second action. The term "responsive to" indicates the causal relationship.

As defined herein, "real-time" means a level of processing responsiveness that a user or system senses as sufficiently immediate for a particular process or determination to be made, or that enables the processor to keep up with some external process.

The term "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

The terms "user" and "individual" refer to a human being.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object-oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the inventive arrangements. In this regard, each block in the flowcharts or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method, comprising:
   generating, by a sound source, a first sequence of sounds that are modulated to perceptually emanate from one or more distinct locations in three-dimensional (3D) space relative to a user, wherein the first sequence of sounds is predetermined to guide the user to perform a first prescribed head movement to mitigate vertigo experienced by the user;
   wherein the user initiates head movements in response to the first sequence of sounds;
   in response to generating the first sequence of sounds, tracking, by at least one sensor, the head movements of the user as the user responds to the first sequence of sounds;
   measuring a heart rate of the user using a photoplethysmography sensor during the head movements;
   comparing the head movements of the user with the first prescribed head movement;
   detecting a condition including a rise in heart rate of the user during the head movements indicating that the user has difficulty performing the first prescribed head movement; and
   in response to the detecting the condition, generating a recommendation to generate a second sequence of sounds corresponding to a second prescribed head movement different from the first prescribed head movement and restricting further generation of the first sequence of sounds.

2. The method of claim 1, further comprising:
   performing a calibration procedure that measures hearing of the user in a left ear of the user and in a right ear of the user independently; and
   generating a left channel head-related transfer function and a right channel head-related transfer function based on the hearing of the user as measured;
   wherein the sound source changes at least one of intensity of the first or second sequence of sounds or speed at which the first or second sequence of sounds is perceived to be moving based on the left channel head-related transfer function and the right channel head-related transfer function.

3. The method of claim 1, wherein
   the first sequence of sounds emulates a gradual movement from one of the one or more distinct locations to another of the one or more distinct locations, the gradual movement calibrated to guide the head movements of the user at a pace likely to avoid inducing or exacerbating the vertigo.

4. The method of claim 1, further comprising:
conveying, by an electronic device, a signal to the user, wherein the signal specifies feedback based on the comparing;
wherein the tracking comprises determining a pace of the head movements of the user, and the feedback, as conveyed, includes guidance based on a comparison of the pace with a predetermined threshold.

5. The method of claim 1, further comprising:
using noise cancellation to substantially cancel ambient sounds in response to determining a measure of loudness of the ambient sounds is likely to impede the user hearing at least one of the first sequence of sounds or the second sequence of sounds.

6. The method of claim 1, wherein the condition includes detecting at least one of the user failing to perform the first prescribed head movement within a predetermined time or failing to complete the first prescribed head movement after a predetermined number of attempts.

7. The method of claim 6, further comprising:
identifying a third head movement by detecting a similarity link between the first prescribed head movement and the third head movement using automated learning; and
restricting generation of a sequence of sounds that is predetermined to guide the user to perform the third head movement.

8. The method of claim 1, further comprising:
displaying one or more extended reality (XR) objects using a display, wherein the XR objects appear to move in a manner predetermined to cause the user to respond in a prescribed manner to mitigate the vertigo experienced by the user.

9. The method of claim 1, further comprising:
detecting a confounding factor based on the measuring.

10. A system, comprising:
a sound source;
a sound transducer operatively coupled with the sound source;
a plurality of sensors including a photoplethysmography sensor; and
a processor operatively coupled to the plurality of sensors and to the sound source, wherein the processor is configured to initiate operations including:
generating a first sequence of sounds from the sound source that are modulated to perceptually emanate from one or more distinct locations in three-dimensional (3D) space relative to a user, wherein the first sequence of sounds is predetermined to guide the user to perform a first prescribed head movement to mitigate vertigo experienced by the user;
wherein the user initiates head movements in response to the first sequence of sounds;
in response to generating the first sequence of sounds, tracking the head movements of the user based on signals generated by the plurality of sensors in response to the head movements as the user responds to the first sequence of sounds;
measuring a heart rate of the user using a photoplethysmography sensor during the head movements;
comparing the head movements of the user with the first prescribed head movement;
detecting a condition including a rise in heart rate of the user during the head movements indicating that the user has difficulty performing the first prescribed head movement; and
in response to the detecting the condition, generating a recommendation to generate a second sequence of sounds corresponding to a second prescribed head movement different from the first prescribed head movement and restricting further generation of the first sequence of sounds.

11. The system of claim 10, wherein the processor is configured to initiate operations further including:
performing a calibration procedure that measures hearing of the user in a left ear of the user and in a right ear of the user independently; and
generating a left channel head-related transfer function and a right channel head-related transfer function based on the hearing of the user as measured;
wherein the sound source changes at least one of intensity of the first or second sequence of sounds or speed at which the first or second sequence of sounds is perceived to be moving based on the left channel head-related transfer function and the right channel head-related transfer function.

12. The system of claim 10, wherein
the first sequence of sounds emulates a gradual movement from one of the one or more distinct locations to another of the one or more distinct locations, the gradual movement calibrated to guide the head movements of the user at a pace likely to avoid inducing or exacerbating the vertigo.

13. The system of claim 10, wherein the processor is configured to initiate operations further including:
conveying, by an electronic device, a signal to the user, wherein the signal specifies feedback based on the comparing;
wherein the tracking comprises determining a pace of the head movements of the user, and the feedback, as conveyed, includes guidance based on a comparison of the pace with a predetermined threshold.

14. The system of claim 10, wherein the processor is configured to initiate operations further including:
using noise cancellation to substantially cancel ambient sounds in response to determining a measure of loudness of the ambient sounds is likely to impede the user hearing at least one of the first sequence of sounds or the second sequence of sounds.

15. The system of claim 10, wherein the condition includes detecting at least one of the user failing to perform the first prescribed head movement within a predetermined time or failing to complete the first prescribed head movement after a predetermined number of attempts.

16. The system of claim 15, wherein the processor is configured to initiate operations further including:
identifying a third head movement by detecting a similarity link between the first prescribed head movement and the third head movement using automated learning; and
restricting generation of a sequence of sounds that is predetermined to guide the user to perform the third head movement.

17. The system of claim 10, wherein the processor is configured to initiate operations further including:
displaying one or more extended reality (XR) objects using a display, wherein the XR objects appear to move in a manner predetermined to cause the user to respond in a prescribed manner to mitigate the vertigo experienced by the user.

18. The system of claim 10, wherein the processor is configured to initiate operations further including:
   detecting a confounding factor based on the measuring.

19. A computer program product, the computer program product comprising:
   one or more computer-readable storage media and program instructions collectively stored on the one or more computer-readable storage media, wherein the program instructions are executable by one or more processors to cause the one or more processors to initiate operations, the operations including:
      generating, by a sound source, a first sequence of sounds that are modulated to perceptually emanate from one or more distinct locations in three-dimensional (3D) space relative to a user, wherein the first sequence of sounds is predetermined to guide the user to perform a first prescribed head movement to mitigate vertigo experienced by the user;
      wherein the user initiates head movements in response to the first sequence of sounds;
      in response to generating the first sequence of sounds, tracking the head movements of the user as the user responds to the first sequence of sounds;
      measuring a heart rate of the user using a photoplethysmography sensor during the head movements;
      comparing the head movements of the user with the first prescribed head movement;
      detecting a condition including a rise in heart rate of the user during the head movements indicating that the user has difficulty performing the first prescribed head movement; and
      in response to the detecting the condition, generating a recommendation to generate a second sequence of sounds corresponding to a second prescribed head movement different from the first prescribed head movement and restricting further generation of the first sequence of sounds.

20. The computer program product of claim 19, wherein the program instructions are executable by the one or more processors to cause the one or more processors to initiate operations further including:
   performing a calibration procedure that measures hearing of the user in a left ear of the user and in a right ear of the user independently; and
   generating a left channel head-related transfer function and a right channel head-related transfer function based on the hearing of the user as measured;
   wherein the sound source changes at least one of intensity of the first or second sequence of sounds or speed at which the first or second sequence of sounds is perceived to be moving based on the left channel head-related transfer function and the right channel head-related transfer function.

* * * * *